United States Patent
Davis et al.

(10) Patent No.: US 7,282,571 B2
(45) Date of Patent: Oct. 16, 2007

(54) METHODS FOR STABILIZING PROTEINS

(75) Inventors: Ashley Stuart Davis, Denver, CO (US); Kim Maria Middleton, Denver, CO (US)

(73) Assignee: Cytoskeleton Inc., Denver, CO (US)

( * ) Notice: Subject to any disclaimer, the term of this patent is extended or adjusted under 35 U.S.C. 154(b) by 25 days.

(21) Appl. No.: 10/771,595

(22) Filed: Feb. 3, 2004

(65) Prior Publication Data

US 2005/0171341 A1 Aug. 4, 2005

(51) Int. Cl.
    *C07K 14/435* (2006.01)
(52) U.S. Cl. .................. 530/402; 530/350; 514/2; 436/172
(58) Field of Classification Search ........ 530/350, 530/345, 802, 402, 395; 514/2; 436/172
    See application file for complete search history.

(56) References Cited

U.S. PATENT DOCUMENTS 4,897,465 A * 1/1990 Cordle et al. ............ 530/387.1

OTHER PUBLICATIONS

Drenckhahn, J. Biol. Chem. 261, 12754, 1986.*
Ballweber, Biochemistry 42, 3060-69, 2003.*
Pollard T. D. (J Cell Biol 99(3), 769-77, 1984).*
Cooper J.A. (Journal of muscle research and cell motility 4(2) 253-62, 1983).*
Blatt, William F. (American Laboratory (Shelton, CT, United States) 21-30, 1969.*
Pardee JD and Spudich JA. 1982. Purification of muscle actin, *Methods in Cell Biology*, 24, 271-288.
Kouyama T and Mihashi K. 1981. Fluorimetry study of N-(1-Pyrenyl)iodoacetamide-labelled F-actin. *Eur. J. Biochem.* 114, 33-38.
Brenner SL and Korn ED. 1983. On the mechanism of actin polymerization subunit exchange at steady state. *J. Biol. Chem.* 258, (8), 5013-5020.
Allison SD, Manning MC, Randolph TW, Middleton K, Davis A, and Carpenter JF. 2000. Optimization of storage stability of lyophilized actin using combinations of disaccharides and dextran. *J. Pharma. Sci.* 89, 199-214.

* cited by examiner

*Primary Examiner*—David Lukton
(74) *Attorney, Agent, or Firm*—Pepper Hamilton LLP

(57) ABSTRACT

In basic research and drug discovery there is a need to provide protein reagents with high activity. In particular proteins that are used in assays must have a good shelf life and a consistent activity. As a system of measuring actin polymerization, pyrene labeled actin was developed in 1983 by Kouyama and Mihashi. However, prior to this disclosure, pyrene actin has been impossible to store for longer than one month because the activity would be lost due to protein denaturation and frozen pyrene actin immediately lost activity. This disclosure relates a method for stabilizing pyrene labeled actin for extended storage times and an optimal storage buffer thus creating a reproducible source of pyrene actin for various assays. Using the processes described herein, pyrene actin has been stored for greater than 3 years at 4° C. which makes it a viable product for retail.

24 Claims, 4 Drawing Sheets

Methods for stabilizing protein

A

B

METHODS FOR STABILIZING PROTEINS

KEYWORDS

Protein, Storage, Assay, Formulation.

ABREVIATIONS

ATP=Adenosine triphosphate, Tris-HCL=Tris(hydroxymethyl)aniomethane hydrochloride, DTT=dithiothreitol.

REFERENCES

1. Pardee J D and Spudich J A. 1982. Purification of muscle actin. *Methods in Cell Biology*, 24, 271-288.
2. Kouyama T and Mihashi K. 1981. Fluorimetry study of N-1-Pyrenyl)iodoacetamide-labelled F-actin. *Eur. J Biochem.* 114, 33-38.
3. Brenner S L and Kom E D. 1983. On the mechanism of actin polymerization subunit exchange at steady state. *J. Biol. Chem.* 258, (8), 5013-5020.
4. Allison S D, Manning M C, Randolph T W, Middleton K, Davis A, and Carpenter J F. 2000. Optimization of storage stability of lyophilized actin using combinations of disaccharides and dextran. *J. Pharma Sci.* 89, 199-214.

FIELD OF THE INVENTION

In basic research and drug discovery there is a need to provide protein reagents with high activity. In particular, proteins that are used in assays must have a good shelf life and a consistent activity.

BACKGROUND OF THE INVENTION

Actin is a major protein of many eukaryotic cells. One of its functions is to polymerize into filaments which are used as structural elements and tracks for moving cargo around the interior of cells. Actin will polymerize in vitro to form 7 nm filaments just like those seen in cells. FIG. 1a indicates, monomers polymerizing to form a helical filament with concomitant hydrolysis of ATP. The initial phase of polymerization is called nucleation (see FIG. 1b), this phase is characterized by monomers initiating a short filament by coalescence. After nucleation a polymerization phase occurs where the majority of filaments are undergoing net polymerization (see FIG. 1b). When the majority of actin has polymerized a phase called steady state exists, in this phase there is an equilibrium between monomer and polymer such that there is a constant polymer mass (see FIG. 1b).

Actin polymerization is tightly regulated in the cell so that inappropriate polymerization does not interfere with normal cellular processes. Scientists need to be able to measure actin polymerization to determine how the regulation works and to develop drugs to actin interacting proteins. As a system of measuring actin polymerization, pyrene labeled actin was developed in 1983 by Kouyama and Mihashi. Essentially, actin is labeled by reacting pyrene iodoacetamide on actin's number 374 amino acid cysteine. The pyrene actin fluorescences when excited by light at 360 nm wavelength. When the actin polymerizes the pyrene moiety moves into a more hydrophobic pocket and its quantum yield increases, thus pyrene actin polymerization is accompanied by a proportionately higher fluorescence signal (see FIG. 2 for an example). However, prior to this disclosure, pyrene actin has been impossible to store for longer than one month because it's activity would be lost due to protein denaturation. Shelf life was a few days for the unpolymerized monomer or a few weeks for the polymers.

The disclosure described here is a method for stabilizing pyrene labeled actin for extended storage times and an optimal storage buffer thus creating a reproducible source of pyrene actin for various assays. Using the processes described herein, we have stored pyrene actin for greater than 3 years at 4° C. which makes it a viable product for retail.

TIMELINE OF THE INVENTIONS

1994—Procedures initiated to produce pyrene actin.
1995—Grant approval to study the effects of freezing and lyophilization on proteins (Small Business Innovative Research Grant from the National Institutes of Health # GM53896), which resulted in a publication concerning the optimization of conditions for actin lyophilization (Allison et al 2000).
1995—The protein concentration prior to rapid freezing was proposed to be a key predictor of pyrene actin activity.
1995—Introduction to Cytoskeleton Inc.'s product line as advertised in 1995 Catalog.
1997—Novel method of pyrene actin reconstitution determined.
2000—Publication of lyophilized actin research (Allison et al. 2000).
2003—The activity of lyophilized pyrene actin determined to be related to the presence of high concentrations of a reducing agent prior to concentration.

DESCRIPTION OF THE FIGURES

FIG. 1a shows a schematic representation of actin polymerization. Monomers coalesce to form short filaments which then elongate with concomitant hydrolysis of ATP. FIG. 1b shows the three phases of polymerization over time (x-axis). The amount of polymer is represented on the y-axis. Nucleation is the coalescence of monomers, this is followed by elongation of the filaments by polymerization, then finally a steady state is achieved which represents an equilibrium between the monomers and polymers.

This figure represents the state of the art before the current invention. Up to this point pyrene actin was recalcitrant to freezing and lyophilization, in contrast to the methods known for unlabeled actin (see Allison et al. 2000). Pyrene actin was prepared as Kouyama and Mihashi 1981 or Brenner and Korn 1983 and sucrose and dextran were added as for un-labeled actin ("Fresh" sample). This was then frozen in the lyophilizer as is normal procedure for protein lyophilization over a period of 1-2 h. These "Frozen" samples were then removed and assayed for activity at the same time as the Fresh samples. The frozen sample has a low fluorescence which does not change much in amplitude indicating little or no polymerization. The Fresh sample shows the normal three phases of actin polymerization. Procedures for measuring pyrene actin activity were as described in "*Determining Pyrene Actin Activity*".

FIG. 3

This figure represents one parameter that was studied in order to produce a stable preparation of pyrene actin. The protein concentration was varied prior to freezing, then the pyrene actin was polymerized in a spectrophotometer to indicate Percent of Polymerization compared to a freshly prepared sample. It was found that from 1 to 10 mg/ml there was very little retention of activity in the frozen samples whether they were rapidly frozen (in liquid nitrogen or dry ice ethanol bath) or slowly frozen (e.g. placed in a −20° C. or −70° C. freezer for 1 h). From 10 mg/ml to 20 mg/ml prior to freezing, the pyrene actin showed a proportionate increase in activity with 20 mg/ml providing >90% activity. At 30 mg/ml even better activity was seen. Rapid freezing was preferable to slow freezing because it resulted in greater retention of activity. Procedures for measuring pyrene actin activity were as described in "*Determining Pyrene Actin Activity*".

FIG. 4

Figure 3:
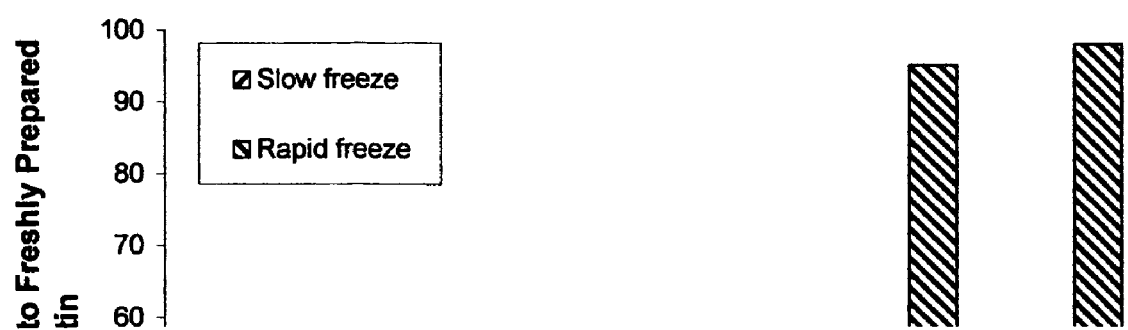
Figure 4:
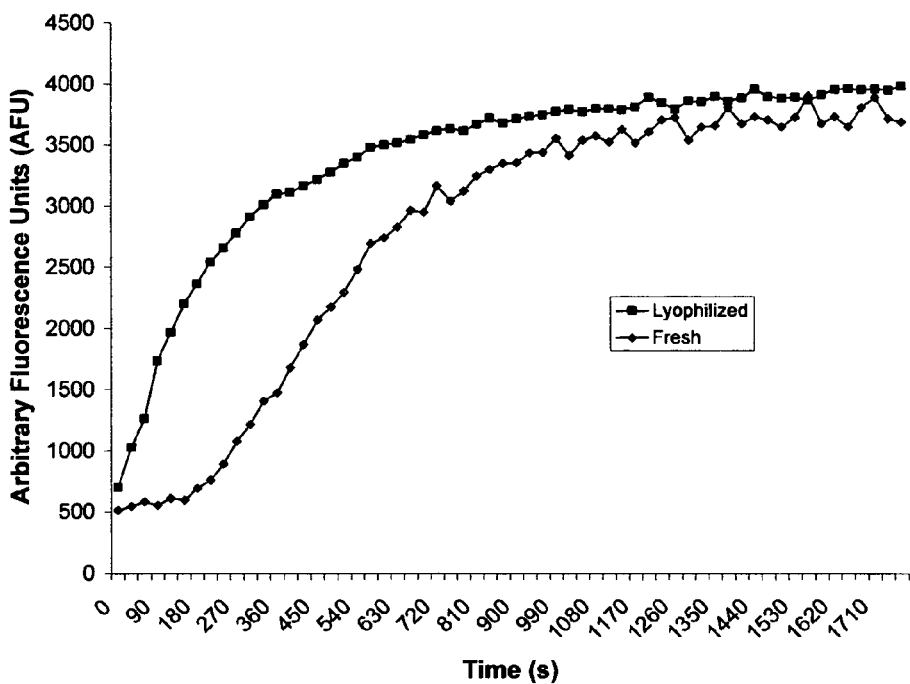
Figure 4:
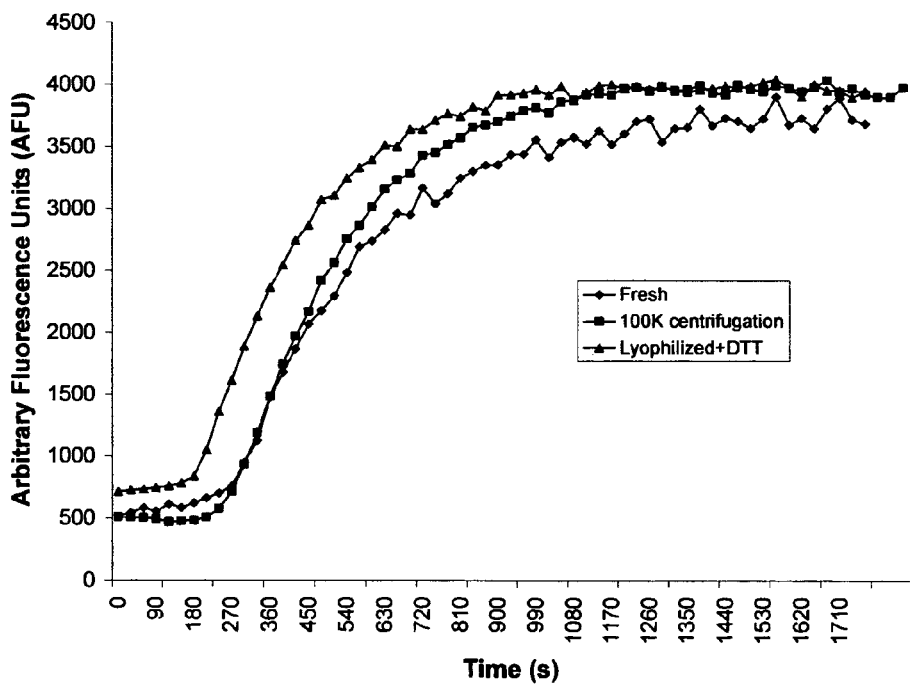

This figure represents the the second novel aspect of this invention, it concerns the quality of the active pyrene actin that was produced in FIG. 3 above. During the freezing and lyophilization process the protein is concentrated and it tends to aggregate into short oligomers of actin which act as nucleating centers during a polymerization assay. This is represented in FIG. 4a as the "Lyophilized" sample. Compared to the "Fresh" sample you will see that it polymerizes quicker, this is due to the nucleating centers elongating and polymerization occurring before the Fresh sample is able to coalesce into its own nucleating centers. We introduced a high concentration of DTT (a reducing agent) in order to reduce aggregation before lyophilization. This resulted in a polymerization profile in FIG. 4b "Lyophilized+DTT" that re-created a nucleation phase and hence improved the characteristics of pyrene actin to reflect more of the Fresh preparation's character. In addition we found that a 100,000×g centrifugation for 2 h which pelleted the remaining oligomers was sufficient to fully reconstitute the Fresh activity profile, see "100K centrifugation" sample. Procedures for measuring pyrene actin activity were as described in "*Determining Pyrene Actin Activity*".

DESCRIPTION OF THE PROCESS

Protocol of Manufacture
1. Actin is made according to Pardee and Spudich 1982.
2. Actin is labeled with pyrene according to Kouyama and Mihashi 1981 or Brenner and Korn 1983.
3. Pyrene actin is then concentrated to 0.2 to 40 mg/ml (novel process) e.g. using an ultrafiltration device.
4. Pyrene actin solution is mixed with sucrose and dextran stabilizing agents as stated for native actin in Allison et al. 1999.
5. Additional reducing agent is added here (novel addition) e.g. 10 mM DTT.
6. Samples are rapidly frozen in liquid nitrogen.
7. Pyrene actin is then lyophilized for 40 h over a temperature starting from −40° C. and ending at +30° C. (novel process).
8. Pyrene actin is then stored at a temperature between −189° C. to +37° C. with less than 5% humidity (novel storage).

Determining Pyrene Actin Activity
1. Resuspend pyrene actin to 0.4 mg/ml in A-buffer (5 mM Tris pH8, 0.2 mM CaCl2, 0.2 mM ATP, also called G-buffer), incubate for 1 h on ice to depolymerize oligomers of actin that form during the preparation process.
2. Place pyrene actin in a cuvette of a fluorescence spectrophotometer and take a background reading using excitation of 360 nm and emission of 407 nm.
3. Add 1/10$^{th}$ volume of polymerization buffer (20 mM MgCl2, 10 mM ATP, 500 mM KCl), mix and place back in the spectrophotometer.
4. Take readings every 30 seconds for 60 min.
5. Active pyrene actin will polymerize to show a 2 to 30 fold increase in fluorescence compared to the starting background value.

Determination of the Degree of Labeling

The following formula is used to determine the number of pyrene molecules per molecule of actin;

$$[A/L\epsilon]/[\text{g of protein per liter/molecular weight of protein}] = \text{moles of dye/moles of protein}$$

where A=the absorbance value of the dye at the absorption maximum wavelength. For pyrene the absorption maximum wavelength is 344 nm. L=length of light path in cm, $\epsilon$=the molar extinction coefficient of the dye or the reagent at the absorption maximum wavelength. For pyrene in methanol this has been determined to be 27,700 cm$^{-1}$ M$^{-1}$. The molar extinction coefficient for pyrene actin at 344 nm was determined to be 22,000 cm$^{-1}$ M$^{-1}$. Molecular weight of actin is 45,000 and the protein was measured using the Precision Red Advanced Protein Assay Reagent (Cytoskeleton Inc. 2003). Usually the labeling stoichiometry is 0.01 to 0.9 pyrenes per actin molecule, preferably it is 0.4 to 0.5 pyrenes per actin molecule.

Example of Varying the Protein Concentration Prior to Lyophiizadon

Prior to this disclosure, the standard conditions for actin lyophilization was stated in Allison et al. 1999, which was 1-3 mg/ml actin in A-buffer plus 5% sucrose and 1% dextran. Sucrose helps stabilize the protein conformation during freezing and dextran is proposed to stabilize the protein structure during long term storage. Unfortunately this does not work for pyrene actin as described next.

Figure 1:
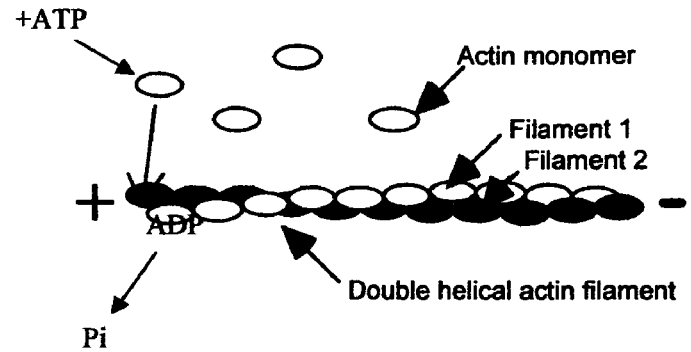
FIG. 1
Figure 1:
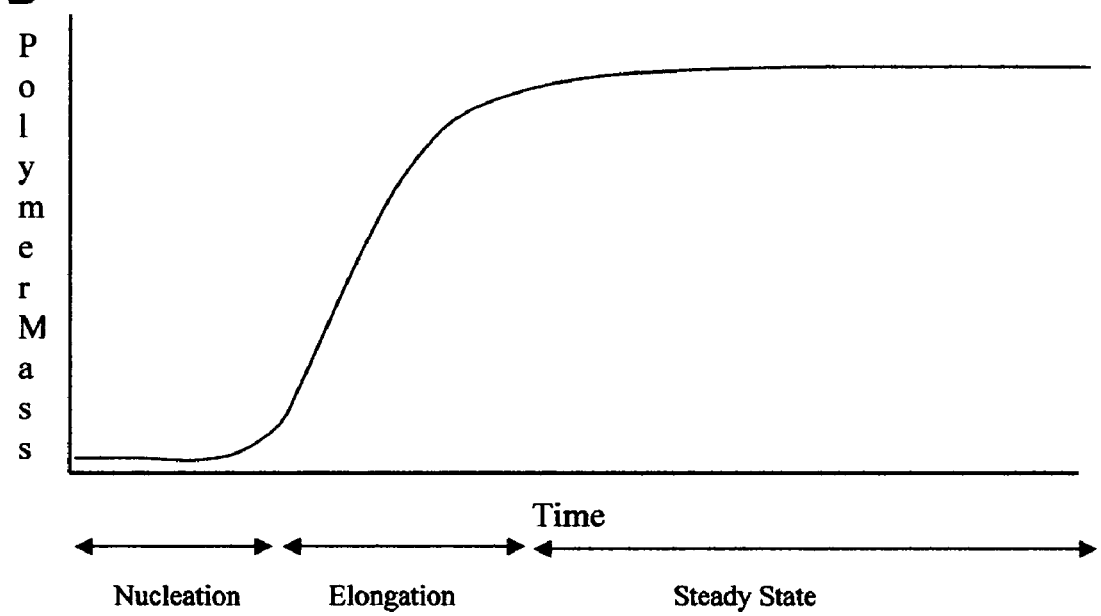
Figure 2:
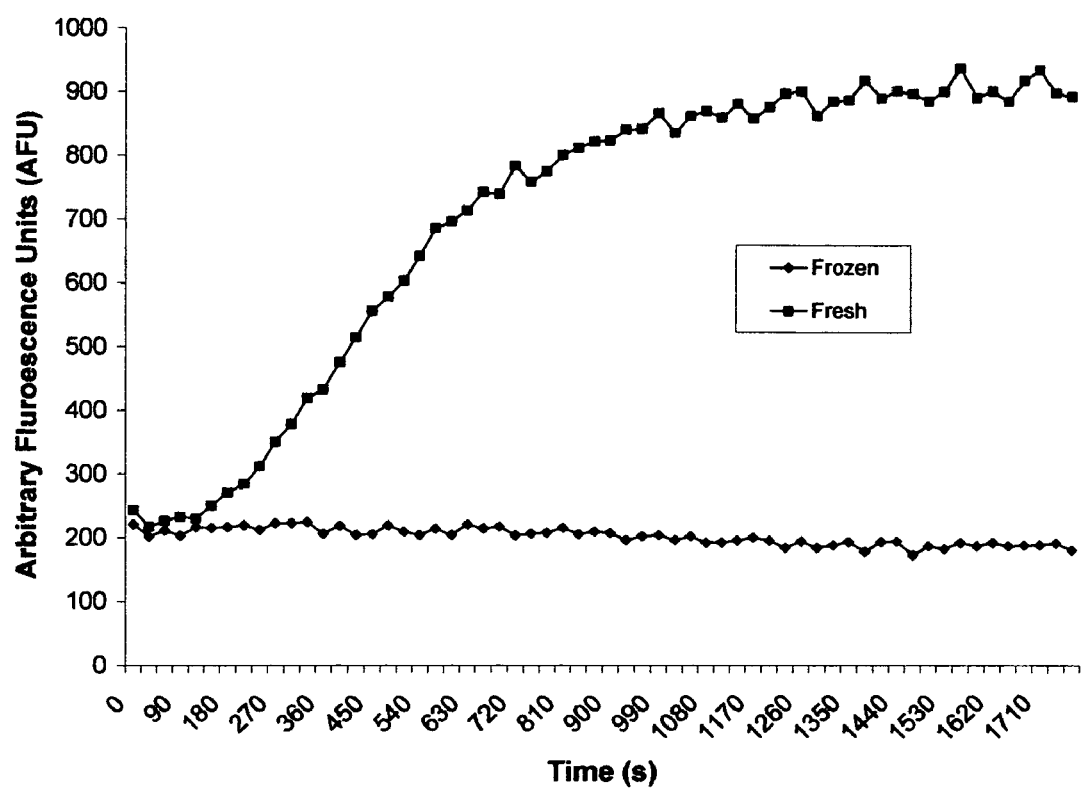
FIG. 2

Pyrene actin was lyophilized in the same way as native actin as per Allison et al. 2000. When the pre-frozen "Fresh", and "Frozen" samples were compared it was found that all the polymerization activity was lost during freezing (see FIG. 2).

We then compared increasing concentrations of pyrene actin for freezing stability with and without rapid freezing (see FIG. 3). It was shown that frozen pyrene actin was only stable when it was concentrated to greater than 10 mg/ml and also when it was rapidly frozen e.g. with liquid nitrogen or dry ice ethanol bath.

The preferable concentration is >20 mg/ml and the preferable freezing rate is less than 5 seconds i.e. placing in liquid nitrogen or dry ice ethanol bath.

Example of Improving the Quality and Activity of Pyrene Actin by using High Concentrations of Reducing Agent.

Prior to this invention, lyophilized pyrene actin showed different polymerization characteristics compared to that prepared fresh as Kouyama and Mihashi 1981 or Brenner and Korn 1983. Essentially as shown in FIG. 4a the "Lyophilized" sample frozen at 20 mg/ml shows a high nucleation potential compared to freshly prepared samples. The leap in logic was the assumption that this was due to monomers linking together during concentration and then chemically crosslinking via the cysteine side chain of unlabeled actin. So we introduced increased concentrations of DTT so the cross linking would be less. As seen in FIG. 4b, the higher concentrations of DTT produced less nucleation and hence re-created a preparation more similar to the freshly prepared pyrene actin. It must be noted that the pyrene actin still had more nucleation potential than freshly prepared material so the process was not completely satisfactory. It is assumed that other more potent reducing compounds, or non-volatile reducing agents or a combination of them would achieve a more satisfactory preparation with near identical characteristics to the freshly prepared sample.

In addition we found that a 100,000×g centrifugation for 2 h which pelleted the remaining oligomers was sufficient to fully reconstitute the Fresh activity profile, see "100K centrifugation" sample in FIG. 4b.

The invention claimed is:

1. A process of preparing a pyrene actin composition comprising:
   a) concentrating a pyrene actin composition;
   b) mixing the concentrated pyrene actin composition with sucrose, a stabilizing agent, and a reducing agent, thereby generating a second pyrene actin composition; and
   c) rapidly freezing the second pyrene actin composition.

2. The process of claim 1, further comprising:
   d) lyophilizing the frozen second pyrene actin composition generated in step c.

3. The process of claim 1 wherein said reducing agent is dithiotbreitol.

4. The process of claim 3, wherein the concentration of dithiothreitol is 10 mM.

5. The process of claim 1, wherein the second pyrene actin composition is rapidly frozen in liquid nitrogen or a dry ice ethanol bath.

6. The process of claim 1, wherein said stabilizing agent is dextran.

7. The process of claim 2, wherein the frozen second pyrene actin composition is lyophilized for 40 hours over a temperature from −40° C. to 30° C.

8. The process of claim 1, wherein said pyrene actin is concentrated to 0.2 to 40 mg/ml.

9. The process of claim 1, wherein said pyrene actin is concentrated to greater than 10 mg/ml.

10. The process of claim 1 wherein said pyrene actin composition of step a) comprises ATP and CaCl$_2$.

11. The process of claim 1 wherein said sucrose is present in the second pyrene actin composition in amount of 5% w/v.

12. The process of claim 1 wherein said stabilizing agent is present in the second pyrene actin composition in an amount of 1% w/v.

13. The process of claim 2 further comprising:
   e) resuspending the lyophilized and frozen second pyrene actin composition in a buffer comprising 5 mM Tris pH 8, 0.2 mM CaCl$_2$, and 0.2 mM ATP, thereby generating a resuspended pyrene actin composition; and
   f) incubating said resuspended pyrene actin composition on ice.

14. The method of claim 13 wherein said resuspended pyrene actin composition is centrifuged.

15. A process of preparing a pyrene actin composition comprising:
   a) concentrating a pyrene actin composition;
   b) mixing the concentrated pyrene actin composition with sucrose, a reducing agent, and optionally a stabilizing agent thereby generating a second pyrene actin composition;
   c) rapidly freezing the second pyrene actin composition; and
   d) lyophilizing the frozen second pyrene actin composition generated in step c.

16. The process of claim 15 wherein said reducing agent is dithiothreitol.

17. The process of claim 15 wherein said stabilizing agent is present, and is dextran.

18. The process of claim 15 further comprising:
   e) resuspending the lyophilized and frozen second pyrene actin composition in a buffer comprising 5 mM Tris pH 8, 0.2 mM CaCl$_2$, and 0.2 mM ATP, thereby generating a resuspended pyrene actin composition; and
   f) incubating said resuspended pyrene actin composition on ice.

19. A method for producing a stabilized form of pyrene actin comprising:
   concentrating pyrene actin to greater than 10 mg/ml and mixing with a reducing agent, and sucrose and dextran stabilizing agents to produce a concentrated pyrene actin;
   rapidly freezing the concentrated pyrene actin to produce a frozen concentrated pyrene actin; and
   lyophilizing the frozen concentrated pyrene actin with a gradient temperature profile from 40° C. to +30° C. to produce the stabilized form of pyrene actin, wherein the stabilized from of pyrene actin, when stored for more than 3 years at 4° C., retains its ability to polymerize with a degree of nucleation that is comparable to that of freshly prepared pyrene actin.

20. The process of claim 19 wherein the concentration of sucrose is 5% and the concentration of dextran is 1%.

21. The process of claim 19 wherein the concentration of pyrene actin prior to freezing is greater than 20 mg/ml.

22. The process of claim 19 wherein the reducing agent is dithiothreitol.

23. The process of claim 19 wherein the lyophilized and frozen concentrated pyrene actin is rehydrated with 5 mM Tris-HCl, 0.2 mM adenosine triphosphate, 0.2 mM CaCl$_2$ and 10 mM dithiothreitol to create a solution of pyrene actin.

24. The method of claim 23 whereby the solution of pyrene actin is polymerized by adding 50 mM KCl, 2 mM MgCl$_2$ and 1 mM adenosine triphosphate.

* * * * *